(12) United States Patent
Merkle et al.

(10) Patent No.: US 7,002,023 B2
(45) Date of Patent: Feb. 21, 2006

(54) METHOD FOR PRODUCING 1 SUBSTITUTED 5-CHLORO-4 METHLY PYRAZOLES

(75) Inventors: Hans Rupert Merkle, Ludwigshafen (DE); Erich Fretschner, Neckarsteinach (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 3 days.

(21) Appl. No.: 10/381,411

(22) PCT Filed: Sep. 28, 2001

(86) PCT No.: PCT/EP01/11259

§ 371 (c)(1),
(2), (4) Date: Mar. 25, 2003

(87) PCT Pub. No.: WO02/26715

PCT Pub. Date: Apr. 4, 2002

(65) Prior Publication Data

US 2004/0102505 A1   May 27, 2004

(30) Foreign Application Priority Data

Sep. 29, 2000   (DE)   .................. 100 48 384

(51) Int. Cl.
*C07D 231/16*   (2006.01)
*C07D 231/18*   (2006.01)
(52) U.S. Cl. .............. 548/366.1; 548/366.1; 548/373.1
(58) Field of Classification Search ............ 548/366.1, 548/373.1; 514/404
See application file for complete search history.

(56) References Cited

U.S. PATENT DOCUMENTS 3,801,584 A   4/1974   Kubo et al.
6,515,139 B1 *   2/2003   Merkle et al. ............ 548/366.1

FOREIGN PATENT DOCUMENTS

| AU | 586 903 | 5/1987 |
|----|---------|--------|
| EP | 350 176 | 1/1990 |
| EP | 350176 A2 * | 1/1990 |
| EP | 366 329 | 5/1990 |
| EP | 366329 A1 * | 5/1990 |

OTHER PUBLICATIONS

Chemical Abstracts XP-002188366.

* cited by examiner

*Primary Examiner*—Kamal A. Saeed
*Assistant Examiner*—Janet L Coppins
(74) *Attorney, Agent, or Firm*—Novak Druce & Quigg LLP; Jason D. Voight

(57) ABSTRACT

The present invention relates to a process for preparing 1-substituted 5-chloro-4-methylpyrazoles of the general formula I

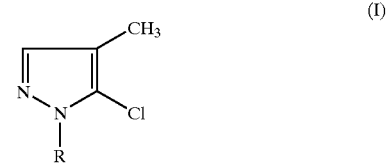

(I)

with the meaning for R stated in claim 1, in which a 4-methylpyrazole of the formula II

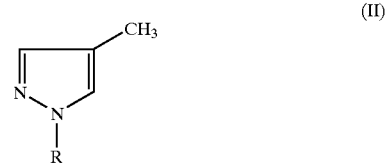

(II)

is reacted with chlorine, the resulting mixture of monochlorinated and dichlorinated product is fractionated by distillation, and subsequently the dichlorinated compound is dehalogenated to compound II and returned to the reaction with chlorine.

11 Claims, No Drawings

METHOD FOR PRODUCING 1 SUBSTITUTED 5-CHLORO-4 METHLY PYRAZOLES

The present invention relates to a process for preparing N-substituted 5-chloro-4-methylpyrazoles of the general formula I

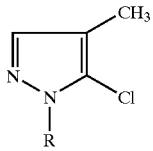

in which
R is $C_1$–$C_8$-alkyl or $C_5$–$C_{10}$-cycloalkyl, each of which optionally has one or more substituents.

1-Alkyl-4-methyl-5-chloropyrazoles are important starting materials for preparing pharmaceuticals and crop protection agents.

EP 0366 329 A1 describes the preparation of 5-halo-4-methylpyrazoles and 3,5-dihalo-4-methylpyrazoles by reacting 4-methylpyrazoles with halogen.

The process described in EP 0366 329 A1 has the disadvantage that the chlorination results in a mixture of monochlorinated and dichlorinated compounds. This means that part of the valuable starting material is lost in the form of the dichlorinated pyrazole, and the yield of 5-chloro-4-methylpyrazole I, based on the 4-methylpyrazole compound II employed, is only moderate. It is an object of the present invention to provide an economic process for preparing 5-chloro-4-methylpyrazoles of the formula I which affords the target compound in better yields based on the 4-methylpyrazole compound employed as starting material.

We have found that this object is achieved by a process in which initially a 4-methylpyrazole compound is reacted with chlorine, the reaction product is fractionated into the monochloropyrazole and dichloropyrazole, and the dichloropyrazole is dehalogenated and returned to the reaction with chlorine.

Accordingly, the present invention relates to a process for preparing 1-substituted 5-chloro-4-methylpyrazoles of the formula I by reacting a 4-methylpyrazole compound of the formula II

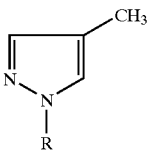

in which R has the abovementioned meanings, with chlorine, resulting in a mixture of compound I and a 1-substituted 3,5-dichloro-4-methylpyrazole compound of the formula III

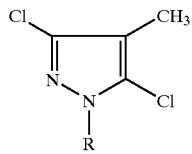

in which R has the aforementioned meanings, wherein the compound III is separated from the compound I, the compound III is dehalogenated to give the compound II, and the latter is reacted anew with chlorine.

The 5-chloro-4-methylpyrazoles I which can be obtained in a high overall yield in the process of the invention can additionally be converted into N-substituted 2-pyrazolin-5-ones, which are likewise valuable intermediates for the preparation of pharmaceuticals and crop protection agents. A further aspect of the present invention is therefore the provision of a process for preparing N-substituted 2-pyrazolin-5-ones starting from 1-substituted 5-chloro-4-methylpyrazoles of the formula I.

The nature of the substituent R is of minor importance in the present invention. Meanings are thus:

$C_1$–$C_8$-Alkyl: a linear or branched alkyl chain with 1 to 8 C atoms, e.g. methyl, ethyl, n-propyl, isopropyl, n-butyl, 2-butyl, isobutyl, tert-butyl, n-pentyl, 2-methylbutyl, 2,2-dimethylpropyl, n-hexyl, 1-methylpentyl, 2-methylpentyl, 1-ethylbutyl, 2-ethylbutyl, n-heptyl, o-octyl and 2-ethylhexyl.

$C_5$–$C_{10}$-Cycloalkyl: mono- or bicyclic hydrocarbon radicals with 5 to 10 carbon atoms, e.g. cyclopentyl, cyclohexyl, cycloheptyl, cyclooctyl, cyclononyl, cyclodecyl, norbornyl, bicyclo[2.2.2]octyl and decahydronaphthyl.

The aforementioned radicals may have one or more substituents. Examples of such radicals are halogen such as fluorine or chlorine, haloalkyl such as trifluoromethyl, pentafluoroethyl and fluoroalkoxy such as trifluoromethoxy and pentafluoroethoxy. Cycloalkyl is also suitable for the radical.

The starting materials of the formula II are known and available to the skilled worker (see, for example, EP 0 366 329 A1 and literature cited therein).

The reaction of the 4-methylpyrazoles II with chlorine takes place by methods customary for a chlorination of pyrazoles, e.g. by the method described in EP 366 329 A1, which is incoporated herein by reference. The chlorination is preferably carried out in an inert organic solvent. Examples of solvents used are halogenated aliphatic hydrocarbons such as 1,2-dichloroethane, dichloromethane, dichloropropane, 1-chloropentane.

The reaction temperature is generally between room temperature and the boiling point of the solvent and is kept in the range from about 40° C. to about 70° C.

Compound II is normally reacted with chlorine in such a way that a sufficient amount of chlorine is added at the required reaction temperature to a reaction vessel containing compound II. Addition can take place either in the form of a chlorine-containing solution, preferably in one of the aforementioned solvents, or else by passing in chlorine gas. Chlorine is mostly employed in excess relative to the pyrazole II, with the aim of complete reaction. This excess is preferably up to 70 mol %, in particular 10–60 mol %. A larger proportion of dichloro compound does not interfere subsequently because in the process of the invention the dichloropyrazole is dehalogenated and returned to the reaction with chlorine.

The reaction mixture resulting from the chlorination is worked up in a conventional way and the mixture of monochloro compound I and dichloro compound III which results in a yield of >95% based on compound II employed, is fractionated, e.g. by fractional distillation, preferably under reduced pressure. This results in compound I in a pure form which can be further processed immediately. According to the invention, compound III, where appropriate mixed with compound I, is then dehalogenated to give compound II.

The dehalogenation of III or of a mixture of compounds I and III takes place by processes conventional for this purpose. A review of various dehalogenation processes is to be found in Chem. Technik 6 (1994) 316–323 and the literature cited therein.

The dehalogenation of a compound III preferably takes place by catalytic hydrogenolysis. The partial pressure of hydrogen is in the range from about 1 bar to about 80 bar, in particular in the range from about 10 bar to about 80 bar, especially in the range from about 10 bar to about 50 bar. The dechlorination normally takes place at elevated temperature, preferably between about room temperature and about 150° C., in particular between about 50° C. and about 100° C. The reaction time depends, as expected, on the chosen reaction conditions and on the compound III used.

The catalysts employed for the hydrogenolysis will normally be transition metals and their compounds or complexes, preferably employing the catalysts in supported form. Particularly preferred transition metals are the metals of group VIII and, very particularly, the platinum metals such as palladium, rhodium and platinum.

Suitable support materials include both inorganic supports such as titanium dioxide, silica gel, silica, zeolites, alumina and organic polymers or activated carbon. In a preferred embodiment of the invention, palladium on activated carbon is used as catalyst.

To trap the hydrogen chloride formed, the hydrogenolysis is preferably carried out in the presence of a suitable base such as a tertiary amine, for example triethylamine, or a basic salt such as an alkali metal acetate or alkaline earth metal acetate, in particular sodium acetate, or such as an alkali metal carbonate or alkali metal bicarbonate, such as sodium carbonate or sodium bicarbonate. Other suitable bases are alkali metal hydroxides such as sodium hydroxide or potassium hydroxide and alkaline earth metal hydroxides such as calcium hydroxide or magnesium hydroxide. Also suitable are alkaline earth metal oxides such as calcium oxide or magnesium oxide. Preferably at least 2 mol of base are employed per mol of the compound III, because two mol of hydrogen chloride must be neutralized.

The dehalogenation is preferably carried out in an organic solvent. Particularly suitable are the starting material II, aliphatic $C_1$–$C_8$-carboxylic acids such as formic acid, acetic acid, ropanoic acid, pivalic acid, butyric acid and mixtures thereof, specially acetic acid, or solvents which are stable under the reaction conditions, such as ethers, for example tetrahydrofuran, ioxane, carboxylic esters such as acetic esters, aromatic hydrocarbons such as toluene or aliphatic hydrocarbons. In a preferred embodiment, glacial acetic acid and/or the starting material II is used as solvent.

Working up the reaction mixture obtained from the dehalogenation by conventional processes results in the 4-methylpyrazole of the formula II, which is then subjected to chlorination anew.

The process of the invention thus makes it possible to convert the pyrazoles of the general formula II into the 5-chloro-4-methylpyrazoles of the general formula I in high yields.

The 5-chloro-4-methylpyrazoles of the formula I are obtained by the process of the invenetion are of particular interest in relation to the synthesis of N-substituted 2-pyrazolin-5-ones of the general formula IV

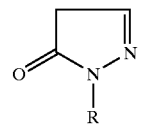

(IV)

in which R is as defined above. This is because the applicant has found that the 4-methyl group in the compounds of the formula I can be degraded and, at the same time, the 5-chloro functionality can be converted into a hydroxyl group. The 5-hydroxypyrazole resulting from this is a tautomer of IV and accordingly rearranges into compound IV or is in equilibrium therewith.

Conversion of the 5-chloro-4-methylpyrazole takes place according to the invention by oxidizing the methyl group in the 4 position to the carboxyl group, and reacting the 4-carboxy-5-chloropyrazole of the formula V obtained in this way and in which R has the aforementioned meanings with a molar excess of alkali metal hydroxide in an aqueous reaction medium at elevated temperature, and subsequently adjusting a pH of $\leq 6$ in the aqueous reaction medium by adding an acid.

Processes for oxidizing aromatic methyl groups to carboxyl groups are known in the prior art, for example from EP 224 094, U.S. Pat. No. 3,801,584 and EP 350 176 A.

N-substituted 5-halo-4-methylpyrazoles are preferably oxidized by the process described in EP-A 350 176 in a simple manner to the carboxylic acids of the formula V.

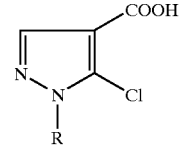

(V)

The oxidation preferably takes place using hydrogen peroxide and/or oxygen. The source of oxygen used is pure oxygen or air, with the partial pressure of the oxygen-containing gas normally being about 1 to 93 bar. The oxidation preferably took place by reacting I with atmospheric oxygen in the presence of a transition metal compound or of a transition metal salt in which the transition metal is present in an oxidation state >0.

Suitable transition metal salts are salts of manganese, cobalt, iron and mixtures thereof, such as iron formate, iron acetate, iron lactate, iron oxalate, iron octylate, iron acetylacetonate, iron chloride, iron bromide, iron iodide, cobalt formate, cobalt acetate, cobalt octylate, cobalt acetylacetonate, cobalt iodide, cobalt carbonate, manganese formate, manganese acetate, manganese octylate, manganese acetylacetonate, manganese chloride, manganese bromide, manganese iodide and manganese carbonate.

The oxidation is preferably carried out in the presence of bromide ions, e.g. in the form of an alkaline earth or alkali metal bromide such as sodium bromide, potassium bromide or ammonium bromide.

The solvents normally used are a lower carboxylic acid such as acetic acid, propionic acid, butyric acid or a lower carboxylic anhydride such as acetic anhydride or propionic anhydride. The reaction temperature is usually in the range from about 20 to about 200° C.

To convert V into the pyrazolone IV in the process of the invention, in a first step a compound of the formula V is reacted with alkali metal hydroxide in molar excess in an aqueous reaction medium. A molar excess of alkali metal hydroxide is ensured with compounds of the general formula V when more than 2 mol of alkali metal hydroxide are employed per mol of compound V. In the first stage, one mol is required for replacing Cl by hydroxyl, and one mol is required for neutralizing the carboxylic acid. It is preferred according to the invention to employ 3 to 20 mol of alkali metal hydroxide and, in particular, 5 to 12 mol of alkali metal hydroxide per mol of compound V. Preferred alkali metal hydroxides are sodium hydroxide and potassium hydroxide, in particular sodium hydroxide.

Suitable aqueous reaction media are both water and mixtures of water and water-miscible organic solvents. The water-miscible organic solvents are preferably inert toward alkali metal hydroxide under the reaction conditions. Examples of suitable organic solvents are $C_1$–$C_4$-alkanols, in particular methanol and ethanol, and additionally dimethyl sulfoxide, tetrahydrofuran, dioxane, glycol, glycerol, diethylene glycol, triethylene glycol and the like. The aqueous reaction medium will usually contain not more than 50% by volume, preferably not more than 30% by volume, and in particular not more than 10% by volume, of a water-miscible organic solvent. In a preferred embodiment of the present invention, water is the sole solvent.

The first reaction step is particularly preferably carried out in an aqueous alkali metal hydroxide solution containing 10 to 50% by weight and, in particular, 20 to 40% by weight of alkali metal hydroxide.

The first reaction step is carried out according to the invention at elevated temperature. Elevated temperature means heating to, normally, at least 50° C. and preferably at least 90° C. The reaction temperature will normally not exceed 200° C. The reaction is very particularly preferably carried out at temperatures in the range from 120 to 200° C.

The first reaction step is carried out under atmospheric pressure or elevated pressure depending on the reaction temperature. At reaction temperatures above 100° C., a reaction pressure of from 1 to 10 bar is normally set up. Typical reaction conditions are, for example with a purely aqueous reaction medium, 150 to 180° C. and 5 to 7 bar.

The reaction will normally lead to almost complete conversion of the starting material V. Conversion means here the transformation of Cl in the pyrazole V into a hydroxyl group or the formation of the corresponding alcoholate. The time taken to reach virtually complete conversion depends, of course, on the chosen reaction conditions and may vary between 0.5 h and 24 h. Typical reaction times in purely aqueous systems are normally in the range from 2 to 10 h.

In the second reaction step, the product obtained in the first reaction step is reacted under acidic conditions. This involves formation of the compound IV with evolution of $CO_2$. The $CO_2$ evolution is attributable to the elimination of the carboxyl group present in the 4 position on the pyrazole ring.

The second reaction stage is normally carried out without isolation of the product formed in the first reaction stage. The second reaction stage is preferably initiated by adding an acid to the reaction mixture from the first reaction stage. It is also possible where appropriate to remove partially or completely the aqueous solvent for the first reaction stage before carrying out the second reaction stage and replace it by a new solvent, preferably an aqueous solvent and, in particular, by water. This procedure is particularly suitable when there has been use in the first stage of an organic solvent which, for example, impedes isolation of the compound IV because of a volatility comparable thereto or in any other way.

The second reaction stage is carried out according to the invention under acidic conditions, i.e. the pH of the reaction mixture in the second reaction stage is at most 6 and is preferably in the range from 1 to 3. The pH is preferably not below 0. The pH is adjusted by adding an acid to the product of the first reaction stage. The acid is preferably given to the aqueous reaction mixture from the first reaction stage. The procedure will normally be such that the reaction mixture from the first reaction stage is cooled to a temperature suitable for the second reaction stage, which is normally in the range from about 0 to 100° C. and is preferably in the range from about 10 to 50° C., and then the acid is added.

Suitable acids are in principle all acids which have an acidic strength sufficient to reach the desired pH. If the second reaction stage is carried out immediately following the first reaction stage, account must be taken of the fact that excess alkali metal hydroxide must be neutralized. For this reason, a strong acid, preferably a mineral acid such as hydrochloric acid, sulfuric acid or phosphoric acid, will be employed to adjust the pH. The acids and, in particular, hydrochloric acid, phosphoric acid and sulfuric acid are preferably employed in a dilute aqueous form.

If the first reaction stage is carried out under pressure, it is advisable to decompress the reactor before neutralization with the acid. The decarboxylation usually starts spontaneously on addition of the acid when the suitable pH is reached. If desired, the reaction conditions can also be maintained for a certain period, which may be from a few minutes up to some hours, to complete the decarboxylation. Compound IV is isolated in a conventional way by working up the reaction mixtures from the second reaction step by conventional workup methods, for example by extractive workup of the liquid reaction mixture with an organic solvent or by removing the solvent and isolating the target compound from the residue obtained thereby. Before the workup it is advisable to neutralize the reaction mixture from the second reaction stage with a base to pH values of $\geq 6$, e.g. pH 6 to 7. Suitable bases are alkali metal hydroxides, alkali metal carbonates, alkali metal bicarbonates, alkaline earth metal carbonates and alkaline earth metal hydroxides. Alkali metal hydroxides and, in particular, sodium hydroxide will normally be employed for the neutralization.

Because of the salt content resulting in the process of the invention, it is frequently advantageous for isolating the compound IV to remove substantially or completely the aqueous reaction medium from the $2^{nd}$ reaction stage, preferably after neutralization, by distillation or by evaporation in vacuo, and to extract the residue with a suitable organic solvent. The solvent chosen for this by the skilled worker will dissolve the desired product but not the salts resulting from the neutralization. Typical organic solvents for the extraction are $C_2$–$C_6$-alcohols such as ethanol, n-propanol, isopropanol, n-butanol, isobutanol, amyl alcohol and isoamyl alcohol, aromatic hydrocarbons such as toluene, ethylbenzene and xylenes. Evaporation of the extract to dryness results in the target compound IV, which can be further purified and worked up in a conventional way.

It is likewise possible to work up the aqueous reaction medium from the $2^{nd}$ reaction stage, preferably after neutralization, by extraction with a polar solvent which is immiscible or of only limited miscibility with water, for example by extraction with a $C_4$–$C_6$-alcohol such as n-butanol, isobutanol, amyl alcohol or isoamyl alcohol, or with one of the aforementioned aromatic hydrocarbons. The extraction can be carried out in portions or continuously.

To illustrate the process of the invention, a typical process method for converting the compounds II into a 2-pyrazolin-5-ones is described below:

The compounds V are dissolved in an aqueous solution of the alkali metal hydroxide. The concentration of the solution is usually in the range from 10 to 50% by weight and is at a level such that 5 to 12 mol of alkali metal hydroxide are present per mol of compound V. This solution is heated in an autoclave to a temperature in the range from 150 to 180° C., setting up a pressure in the range from 5 to 7 bar. The reaction temperature is maintained for 2 to 10 hours. After cooling to room temperature and decompression to atmospheric pressure, a sufficient amount of mineral acid to adjust the pH is added. The pH is preferably in the range from 0 to 6 and, in particular, in the range from 1 to 3. Spontaneous $CO_2$ evolution occurs at this point. A base is then used to neutralize to pH 6 to 7. The reaction mixture is evaporated to dryness in vacuo, and the solid residue is extracted, for example in a Soxhlet apparatus, with a suitable solvent. Evaporation of the solvent results in the N-substituted 2-pyrazolin-5-one of the formula IV in high yield and purity. In place of evaporation/extraction it is possible to isolate the compound IV from the aqueous reaction mixture after neutralization to pH 6 to 7 also by extraction with a suitable solvent, e.g. isobutanol or toluene.

To illustrate the process of the invention, a typical process method for converting the compounds of the general formula II into the N-substituted 5-chloro-4-methylpyrazoles of the general formula I, subsequent oxidation thereof to a compound of the general formula V, and the conversion of the compounds V into the N-substituted 2-pyrazolin-5-ones of the general formula IV is described below. These examples serve only for illustration and are not to be regarded as restrictive.

EXAMPLE 1

Chlorination of 1,4-dimethylpyrazole 190 g (2.67 mol) of chlorine were passed into a solution of 192 g (2.0 mol) of 1,4-dimethylpyrazole and 800 g of 1,2-dichloroethane over the course of 2 h. The temperature rose to 60° C. and could be kept at 60° C. by cooling with ice. While cooling, the resulting reaction mixture was neutralized at 25° C. with 650 g (2.43 mol) of 15% strength aqueous sodium hydroxide solution. After phase separation, the organic phase was distilled to afford 170.1 g (1.3 mol) of 5-chloro-1,4-dimethylpyrazole of boiling point (120) 105° C. and a purity of 99.7% (GC) and 99.3 g (0.6 mol) of 3,5-dichloro-1,4-dimethylpyrazole of boiling point (15) 85° C. and a purity of 99.5% (GC). The yields of 5-chloro-1,4-dimethylpyrazole and 3,5-dichloro-1,4-dimethylpyrazole resulted in an overall yield of 95% based on 1,4-dimethylpyrazole.

EXAMPLE 2

Dehalogenation of 3,5-dichloro-1,4-dimethylpyrazole in glacial acetic acid 12.5 g (0.075 mol) of 3,5-dichloro-1,4-dimethylpyrazole with a purity of 99.5%, 150 g of 100% pure acetic acid, 12.3 g (0.15 mol) of sodium acetate and 6.3 g of 10% Pd/C catalyst were heated to 60° C. in a 350 ml stirred autoclave. 30 bar of hydrogen were injected at this temperature. The reaction started immediately and hydrogen uptake was complete after about 3 h. The autoclave was allowed to cool to 25° C. and was decompressed, and the catalyst and the produced sodium chloroid were filtered off. Distillation of the filtrate afforded 6.86 g of 1,4-dimethylpyrazole of boiling point 151° C. and a purity of 99.7% (GC). This corresponds to a yield of 95% of theory.

EXAMPLE 3

Dehalogenation of 3,5-dichloro-1,4-dimethylpyrazole in 1,4-dimethylpyrazole in the presence of sodium acetate 16.6 g (0.1 mol) of 3,5-dichloro-1,4-dimethylpyrazole with a purity of 99.5%, 50 g of 99.8% pure 1,4-dimethylpyrazole, 16.4 g (0.2 mol) of sodium acetate and 6.4 g of 30% Pd/C catalyst were heated to 80° C. in a 350 ml stirred autoclave. 40 bar of hydrogen were injected at this temperature. Hydrogen uptake was complete after about 6 h. The autoclave was allowed to cool to 25° C. and was decompressed, and the catalyst and produced sodium chloride were filtered off. Distillation of the filtrate afforded 59 g of 1,4-dimethylpyrazole of boiling point 151° C. and a purity of 99.8%. Subtracting the 50 g of 1,4-dimethylpyrazole employed as solvent, this corresponds to a yield of 93.6% of theory.

EXAMPLE 4

Dehalogenation of 3,5-dichloro-1,4-dimethylpyrazole in 1,4-dimethylpyrazole in the presence of sodium hydroxide solution 16.6 g (0.1 mol) of 3,5-dichloro-1,4-dimethylpyrazole with a purity of 99.5%, 50 g of 99.8% pure 1,4-dimethylpyrazole, 16.0 g (0.2 mol) of 50% by weight sodium hydroxide solution and 6.4 g of 30% Pd/C catalyst were heated to 80° C. in a 350 ml stirred autoclave. 40 bar of hydrogen were injected at this temperature. Hydrogen uptake was complete after about 6 h. The autoclave was allowed to cool to 25° C. and was decompressed, and the catalyst and produced sodium chloride were filtered off. Distillation of the filtrate afforded 58.7 g of 1,4-dimethylpyrazole of boiling point 151° C. and a purity of 99.8%. Subtracting the 50 g of 1,4-dimethylpyrazole employed as solvent, this corresponds to a yield of 90.0% of theory.

EXAMPLE 5

Dehalogenation of 3,5-dichloro-1,4-dimethylpyrazole in 1,4-dimethylpyrazole in the presence of calcium hydroxide 16.6 g (0.1 mol) of 3,5-dichloro-1,4-dimethylpyrazole with a purity of 99.5%, 50 g of 99.8% pure 1,4-dimethylpyrazole, 7.4 g (0.1 mol) of calcium hydroxide, 8 ml of water and 6.4 g of 30% Pd/C catalyst were heated to 80° C. in a 350 ml stirred autoclave. 40 bar of hydrogen were injected at this temperature. Hydrogen uptake was complete after about 6 h. The autoclave was allowed to cool to 25° C. and was decompressed, and the catalyst and produced calcium chloride were filtered off. Distillation of the filtrate afforded 58.2 g of 1,4-dimethylpyrazole of boiling point 151° C. and a purity of 99.7%. Subtracting the 50 g of 1,4-dimethylpyrazole employed as solvent, this corresponds to a yield of 84.6% of theory.

EXAMPLE 6

Dehalogenation of 3,5-dichloro-1,4-dimethylpyrazole in 1,4-dimethylpyrazole in the presence of calcium oxide 16.6 g (0.1 mol) of 3,5-dichloro-1,4-dimethylpyrazole with a purity of 99.5%, 50 g of 99.8% pure 1,4-dimethylpyrazole, 5.6 g (0.1 mol) of calcium oxide, 8 ml of water and 6.4 g of 30% Pd/C catalyst were heated to 80° C. in a 350 ml stirred autoclave. 40 bar of hydrogen were injected at this temperature. Hydrogen uptake was complete after about 6 h. The autoclave was allowed to cool to 25° C. and was decompressed, and the catalyst and produced calcium chloride were filtered off. Distillation of the filtrate afforded 57.6 g of 1,4-dimethylpyrazole of boiling point 151° C. and a purity of 99.7%. Subtracting the 50 g of 1,4-dimethylpyrazole employed as solvent, this corresponds to a yield of 78.4% of theory.

EXAMPLE 7

Chlorination of 1-ethyl-4-methylpyrazole 167.7 g (2.36 mol) of chlorine were passed into a solution of 165 g (1.5 mol) of 1-ethyl-4-methylpyrazole and 625 g of 1,2-dichloroethane over the course of 2 h. The temperature rose to 60° C. and could be kept at 60° C. by cooling with ice. While cooling, the resulting reaction solution was neutralized at 25° C. with 533.9 g (2.0 mol) of 15% strength aqueous sodium hydroxide solution. After phase separation, the organic phase was distilled to afford 122.1 g (0.843 mol) of 5-chloro-1-ethyl-4-methylpyrazole of boiling point (200) 118° C. and a purity of 99.8% (GC) and 109.1 g (0.61 mol) of 3,5-dichloro-1-ethyl-4-methylpyrazole of boiling point (200) 154° C. and a purity of 99.6%. This corresponds to a yield of 96.6% of theory based on 1-ethyl-4-methylpyrazole.

EXAMPLE 8

Dehalogenation of 3,5-dichloro-1-ethyl-4-methylpyrazole in glacial acetic acid 18.0 g (0.1 mol) of 3,5-dichloro-1-ethyl-4-methylpyrazole with a purity of 99.6%, 100 g of 100% pure acetic acid, 16.4 g (0.2 mol) of sodium acetate and 8.4 g of 10% Pd/C catalyst were heated to 80° C. in a 350 ml stirred autoclave. 20 bar of hydrogen were injected at this temperature. The reaction started immediately and hydrogen uptake was complete after about 2 h. The autoclave was allowed to cool to 25° C. and was decompressed, and the catalyst and the produced sodium chloride were filtered off. Distillation of the filtrate afforded 10.3 g of 1-ethyl-4-methylpyrazole of boiling point 158° C. and purity 99.6% (GC). This corresponds to a yield of 93.4% of theory.

EXAMPLE 9

Dehalogenation of 3,5-dichloro-1-ethyl-4-methylpyrazole in 1-ethyl-4-methylpyrazole 18.0 g (0.1 mol) of 3,5-dichloro-1-ethyl-4-methylpyrazole with a purity of 99.6%, 50 g of 1-ethyl-4-methylpyrazole with a purity of 99.8%, 16.4 g (0.2 mol) of sodium acetate and 6.4 g of 30% Pd/C catalyst were heated to 80° C. in a 350 ml stirred autoclave. 30 bar of hydrogen were injected at this temperature. Hydrogen uptake was complete after about 4 h. The autoclave was allowed to cool to 25° C. and was decompressed, and the catalyst and the produced sodium chloride were filtered off. Distillation of the filtrate afforded 60.4 g of 1-ethyl-4-methylpyrazole of boiling point 158° C. and purity 99.7%; subtracting the 50 g of 1-ethyl-4-methylpyrazole employed, this corresponds to a yield of 93.6% of theory.

EXAMPLE 10

Oxidation of 5-chloro-1,4-dimethylpyrazole 43.1 g (0.33 mol) of 5-chloro-1,4-dimethylpyrazole, 2.5 g (0.01 mol) of cobalt(II) acetate tetrahydrate, 0.66 g (2.68 mmol) of manganese(II) acetate tetrahydrate, 2.0 g (19.4 mmol) of 40 sodium bromide and 180 g (3.0 mol) of 100% pure acetic acid were heated to 130° C. in a 350 ml stirred autoclave. 20 bar of oxygen were injected at this temperature. The reaction started immediately. Oxygen was reinjected several times. After about 5 hours there was no further consumption of oxygen. The autoclave 45 was cooled to room temperature and decompressed. The resulting reaction mixture was concentrated in a rotary evaporator. The resulting residue was recrystallized from 300 ml of 20% by weight aqueous acetic acid. Drying resulted in 44.1 g of 5-chloro-1-methyl-4-pyrazolecarboxylic acid with a purity of 99.2% (HPLC). This corresponds to a yield of 82.6% of theory. The melting point was 197° C.

EXAMPLE 11

Oxidation of 5-chloro-1-ethyl-4-methylpyrazole

The batch size and procedure corresponded to Example 10. 47.7 g (0.33 mol) of 5-chloro-1-ethyl-4-methylpyrazole were employed. Drying resulted in 46.0 g of 5-chloro-1-ethyl-4-pyrazolecarboxylic acid with a purity of 99.5% (HPLC). This corresponds to a yield of 79.5% of theory. The melting point was 208° C.

EXAMPLE 12

Oxidation of 5-chloro-1,4-dimethylpyrazole 26.1 g (0.2 mol) of 5-chloro-1,4-dimethylpyrazole, 6.6 g (0.026 mol) of cobalt(II) acetate tetrahydrate, 6.0 g (0.035 mol) of 47% strength hydrobromic acid, 2.0 g (0.017 mol) of 30% strength hydrogen peroxide and 240 g (4.0 mol) of 100% pure acetic acid were heated to 90° C. in a 350 ml stirred autoclave. 30 bar of oxygen were injected at this temperature. The reaction started immediately. Oxygen was reinjected several times. Oxygen consumption ceased after about 6 hours. The autoclave was cooled to room temperature and decompressed. The resulting reaction mixture was concentrated in a rotary evaporator. Recrystallization from 150 ml of 20% by weight aqueous acetic acid afforded after drying 26.5 g of 5-chloro-1-methyl-4-pyrazolecarboxylic acid with a purity of 98.7% (HPLC). This corresponds to a yield of 81.5% of theory. The melting point was 195° C.

EXAMPLE 13

Preparation of 1-methyl-2-pyrazolin-5-one 10 g (0.0623 mol) of 5-chloro-1-methyl-4-pyrazolecarboxylic acid were dissolved in 100 g of 25% by weight sodium hydroxide solution (=0.623 mol) in a 250 ml autoclave. The solution was heated at 175° C. for 6 h. The pressure rose to 6 bar during this. Cooling was followed by decompression to atmospheric pressure. The reaction mixture was then adjusted to pH 1.5 with 60% by weight sulfuric acid. $CO_2$ evolution occurred during this. After a few minutes, the pH was adjusted to 6.5 with 25% by weight sodium hydroxide solution, and the resulting solution was evaporated to dryness in vacuo. The solid residue was transferred into a 45 Soxhlet apparatus and extracted continuously with ethanol. Removal of the ethanol by distillation in vacuo resulted in 5.7 g of a target compound with a purity of 98.9% (determined by gas chromatography). The melting point was 113° C. This corresponds to a yield of 92.3% of theory. The product was identified through a mixed melting point with an authentic sample.

EXAMPLE 14

Preparation of 1-ethyl-2-pyrazolin-5-one=5-hydroxy-1-ethylpyrazole 4 g of 5-chloro-1-ethyl-4-pyrazolecarboxylic acid were dissolved in 40 g of 25% by weight sodium hydroxide solution and reacted in analogy to the procedure described in Example 1. The reaction temperature in the first reaction stage was 170° C., and the reaction pressure was 7.5 bar. The reaction lasted 8 h. Working up in the manner described for Example 1 resulted in 2.3 g of the target compound with a purity of 99.7% (determined by gas chromatography). This corresponds to a yield of 89.4% of theory. The melting point was 88° C. The product was identified by a mixed melting point with an authentic sample.

EXAMPLE 15

Preparation of 1-methyl-2-pyrazolin-5-one, workup by liquid/liquid extraction 10 g of 5-chloro-1-methylpyrazole-4-carboxylic acid were reacted as in Example 1 initially with 100 g of 25% by weight sodium hydroxide solution and subsequently under acidic conditions. After the acidic reaction mixture had been neutralized to pH 6.5 with 25% by weight sodium hydroxide solution, the reaction mixture was transferred into a liquid/liquid extractor and extracted with isobutanol at the boiling point of the solvent. After isolation of the organic phase and removal of the isobutanol by distillation, 5.8 g of 1-methyl-2-pyrazolinone remained (GC purity: 98.1%). The melting point was 112° C. The yield was 92.5% of theory.

We claim:

1. A process for preparing 1-substituted 5-chloro-4-methylpyrazoles of the formula I

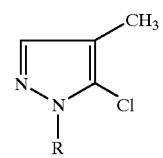

in which
R is $C_1$–$C_8$-alkyl or $C_5$–$C_{10}$-cycloalkyl, each of which optionally has one or more substituents,
by reacting a 4-methylpyrazole of the formula II

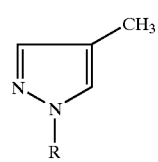

in which
R has the abovementioned meanings, with chlorine, resulting in a mixture of compound I and a 1-substituted 3,5-dichloro-4-methylpyrazole compound III

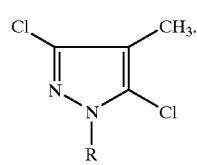

in which
R has the aforementioned meanings, wherein the compound III is separated from the compound I, the compound III is dehalogenated to give the compound II, and the latter is returned to the reaction of II with chlorine.

2. A process as claimed in claim 1, wherein the dehalogenation is carried out with hydrogen in the presence of palladium as catalyst.

3. A process as claimed in claim 2, wherein the catalyst is palladium supported on activated carbon.

4. A process as claimed in claim 1, wherein compound III is combined before the dehalogenation with the compound II to be chlorinated.

5. A process for preparing 1-substituted pyrazolones of the formula IV

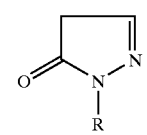

which comprises preparing in a first reaction step a 1-substituted 5-chloro-4-methylpyrazole of the formula I by a process as claimed in claim 1, subsequently oxidizing the 4-methyl group in the compound I to a carboxyl group, reacting the 4-carboxy-5-chloropyrazole of the formula V obtained in this way

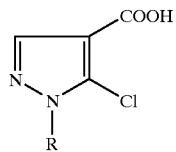

(V)

in which

R has the meanings stated in claim 1, with a molar excess of alkali metal hydroxide in an aqueous reaction medium at elevated temperature, and subsequently adjusting a pH of ≦6 in the aqueous reaction medium by adding an acid.

6. A process as claimed in claim 5, wherein the compound of the formula V is reacted with at least 3 mol of alkali metal hydroxide based on 1 mol of the compound V.

7. A process as claimed in claim 5, wherein the reaction with aqueous alkali metal hydroxide is carried out at a temperature above 90° C.

8. A process as claimed in claim 5, wherein the acid is added at a temperature in the range from 0 to 100° C.

9. A process as claimed in claim 5, wherein the dehalogenation is carried out with hydrogen in the presence of palladium as catalyst.

10. A process as claimed in claim 5, wherein the catalyst is palladium supported on activated carbon.

11. A process as claimed in claim 5, wherein compound III is combined before the dehalogenation with the compound II to be chlorinated.

* * * * *